United States Patent
Heindl et al.

(10) Patent No.: US 10,421,997 B2
(45) Date of Patent: Sep. 24, 2019

(54) MOLECULAR DYNAMIC SEQUENCING

(71) Applicants: ROCHE DIAGNOSTICS OPERATIONS, INC., Indianapolis, IN (US); DYNAMIC BIOSENSORS GMBH, Martinsried/Planegg (DE)

(72) Inventors: Dieter Heindl, Munich (DE); Andreas Langer, Munich (DE); Ulrich Rant, Munich (DE); Ralf Strasser, Munich (DE); Michael Schraeml, Penzberg (DE)

(73) Assignee: Roche Diagnostics Oeprations, Inc., Indianapolis, IN (US)

( * ) Notice: Subject to any disclaimer, the term of this patent is extended or adjusted under 35 U.S.C. 154(b) by 364 days.

(21) Appl. No.: 15/121,220

(22) PCT Filed: Feb. 3, 2015

(86) PCT No.: PCT/EP2015/052131
§ 371 (c)(1),
(2) Date: Aug. 24, 2016

(87) PCT Pub. No.: WO2015/128157
PCT Pub. Date: Sep. 3, 2015

(65) Prior Publication Data
US 2017/0009285 A1  Jan. 12, 2017

(30) Foreign Application Priority Data
Feb. 25, 2014  (EP) .................................. 14000670

(51) Int. Cl.
*C12Q 1/6869* (2018.01)
*G01N 27/327* (2006.01)

(52) U.S. Cl.
CPC ....... *C12Q 1/6869* (2013.01); *G01N 27/3276* (2013.01)

(58) Field of Classification Search
None
See application file for complete search history.

(56) References Cited

U.S. PATENT DOCUMENTS

| | | |
|---|---|---|
| 6,306,607 B2 | 10/2001 | Williams |
| 6,869,764 B2 | 3/2005 | Williams et al. |
| 6,936,702 B2 | 8/2005 | Williams et al. |

(Continued)

FOREIGN PATENT DOCUMENTS

| | | |
|---|---|---|
| EP | 1588755 A1 | 10/2005 |
| EP | 2192401 A1 | 6/2010 |

(Continued)

OTHER PUBLICATIONS

Palecek, Emil, Surface-attached molecular beacons light the way for DNA sequencing, TRENDS in Biotechnology, Feb. 2004, pp. 55-58, vol. 22, No. 2.

(Continued)

*Primary Examiner* — Kaijiang Zhang
(74) *Attorney, Agent, or Firm* — Olga Kay

(57) ABSTRACT

The present invention relates to a method of identifying a nucleotide at a defined position and determining the sequence of a target polynucleotide using an electro-switchable biosensor, as well as devices comprising an electro-switchable biosensor and uses thereof.

12 Claims, 6 Drawing Sheets

(56) References Cited

U.S. PATENT DOCUMENTS

Figure 1:
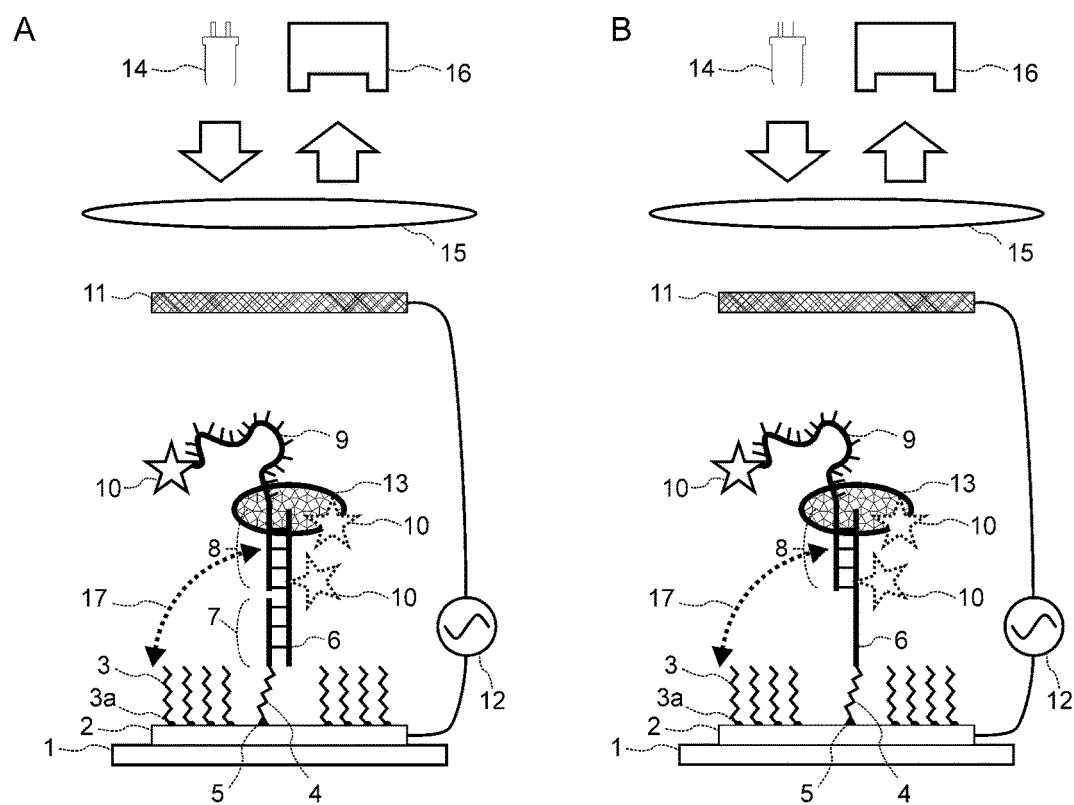

| | | |
|---|---|---|
| 7,462,468 B1 | 12/2008 | Williams et al. |
| 2005/0042633 A1 | 2/2005 | Williams |
| 2005/0266456 A1 | 12/2005 | Williams et al. |
| 2006/0063173 A1 | 3/2006 | Williams et al. |
| 2013/0096013 A1* | 4/2013 | Esfandyarpour et al. ............ C12Q 1/6869 506/2 |

FOREIGN PATENT DOCUMENTS

| | | |
|---|---|---|
| EP | 2434021 A1 | 3/2012 |
| WO | WO2004087303 A1 | 10/2004 |

OTHER PUBLICATIONS

Rant et al, Switchable DNA interfaces for the highly sensitive detection of label-free DNA targets, Proceedings of the National Academy of Science, Oct. 10, 2007, pp. 17364-17369, vol. 104, No. 44.

Stengel et al, Surface plasmon field-enhanced fluorescence spectroscopy studies of primer extension reactions, Nucleic Acids Research, Apr. 2005, e69 (10 pp.), vol. 33, No. 10.

Agrawal, S., Functionalization of Oligonucleotides with Amino Groups and Attachment of Amino Specific Reporter Groups, Methods in Molecular Biology, 1994, 93-120, vol. 26—Chapter 3, Humana Press, Totowa, New Jersey.

Dueholm K.L. et al, 1994, Synthesis of Peptide Nucleic Acid Monomers Containing the Four Natural Nucleobases: Thymine, Cytosine, Adenine, and Guanine and Their Oli-gomerization, J. Org. Chem. 59, 5767-5773.

Gait, M. J., A Practical Approach, Oligonucleotide synthesis, (1984), pp. 1-2.

Innis, M. A. et al., A Guide to Methods and Applications, PCR Protocols, (1990), pp. 1-2.

Kujpers W.H.A. et al., 1994, Synthesis of well-defined phosphate-methylated DNA fragments: the application of potassium carbonate in methanol as deprotecting reagent, Nucleic Acids Research 18(17), 5197-52017.

Lahann et al., 2003, a reversibly switching surface. Science, 299(5606): 371-374.

Maxam and Gilbert (1980) in Grossman and Moldave (eds.), "Sequencing end-labeled DNA with base-specific chemical cleavages", Academic Press, New York, Methods in Enzymology 654:499-560.

Niedringhaus et al., 2011, "Landscape of next-generation sequencing technologies". Anal. Chem. 83:4327-4343.

Sambrook et al, Molecular Cloning a Laboratory Manual, Molecular Cloning: A Laboratory Manual, 1989, Cover, Bibliography, Table of Contents, Third Edition, Cold Spring Harbor Laboratory Press.

Tijssen, P. et al., Hybridization with Nucleic Acid Probes, Laboratory Techniques in Biochemistry and Molecular Biology, (1993), pp. 19-78, vol. 24, Chapter 2.

* cited by examiner

A

```
3'          [40nt mixed seq]-[40nt mixed seq, tb-seq]-Cy3
            ||||||||||||||||
5' HS-(CH2)6-[40nt compl. seq]
```

B

MOLECULAR DYNAMIC SEQUENCING

The present invention relates to a method of identifying a nucleotide at a defined position and determining the sequence of a target polynucleotide using an electro-switchable biosensor, as well as devices comprising an electro-switchable biosensor and uses thereof.

DNA sequencing is a technology widely used in the field of biotechnology. For various applications, like individual genome sequencing, detection of single nucleotide polymorphisms, metagenomics studies and sequencing of various organisms of interest, the known technologies are insufficient. Also, there is a general need for DNA sequencing methods which are quick and cost-effective. In this respect, DNA methods for sequencing based on sequencing by synthesis (SBS) have been described (see Niedringhaus et al., 2011, Anal. Chem. 83:4327-4343). Such methods have the advantage that no PCR reaction is performed. However, the described methods based on sequencing by synthesis suffer from disadvantages: the described use of pyrophosphate released by dNTPs for detection requires that several enzymes have to be added. Alternatively, a pH change can be detected in such known methods. However, such pH detection methods are comparably expensive and complicated. Also, the known methods make use of soluble and solubilized substrates for the detection of an elongation event. Therefore, such methods have to be performed in a well-format in order to maintain spatial separation.

Therefore, there is a need for methods for identifying a nucleotide at a defined position of a target polynucleotide, for example for determining single nucleotide polymorphisms (SNPs), and for DNA sequencing, which methods allow quick and robust sequencing and identification of a nucleotide at a defined position of a target polynucleotide, and which preferably do not require a washing step for the removal of a signaling entity and which preferably allow detection of a non-diffusing signal not requiring a well. This problem is solved by the present invention.

In one embodiment, the present invention relates to a method of identifying a nucleotide at a defined position of a target polynucleotide, the method comprising
a) providing an electro-switchable biosensor comprising
   a primer capable of forming a hybridized polynucleotide with the target polynucleotide, wherein the primer is bound via a linker to a electro-switchable surface, and
   means for applying an alternating current voltage and determining the velocity of the hybridized polynucleotide's movement in the electric field;
b) contacting the primer, under conditions conducive to the formation a hybridized polynucleotide and the elongation of the primer, with the target polynucleotide and a polymerase capable of elongating the primer;
c) contacting the primer with one or more nucleoside triphosphate containing identical nucleobases of one type, wherein
   the nucleoside triphosphate is incorporated into the hybridized polynucleotide and the primer is elongated, if its nucleobase is complementary to a nucleobase at the corresponding position on the target polynucleotide, and
   the nucleoside triphosphate is not incorporated into the hybridized polynucleotide and the primer is not elongated, if its nucleobase is not complementary to a nucleobase at the corresponding position on the target polynucleotide;
d) applying an alternating current voltage to the surface and determining the velocity of the hybridized polynucleotide's movement in the generated electric field, wherein a decreased velocity is indicative of the incorporation of the nucleoside triphosphate; and
e) if the nucleoside triphosphate is not incorporated into the hybridized polynucleotide, repeating steps b) and c) with one or more nucleoside triphosphates containing identical nucleobases of a type different from that used in previous step(s) c), until elongation is detected,
thus identifying the nucleotide at the corresponding position of the target polynucleotide.

The prior art discloses methods for evaluating label-free target molecules in which a marker is modified into a charged probe molecule, the probe molecule is fixed to an electrode and driven by an electrical field, and the drive state is monitored by signals from the marker (EP 2 192 401). When a target molecule binds specifically with the probe molecule, the drive state of the probe changes, which change is evaluated by the marker that has been modified into a probe (WO 2004/087303). The principle underlying this technique is to monitor changes in the signals from the marker that arise due to the changes in the distance between the marker attached to the end of the probe molecule and the substrate as the electrically charged probe molecule is attracted to or repelled by the electric field. So long as the driving frequency is in a frequency range (up to about 1 MHz) that allows formation of an electric double layer as the source of the electric field, evaluation of the target molecule is possible by monitoring signals from the marker that are synchronous with the driving potential.

Figure 4:
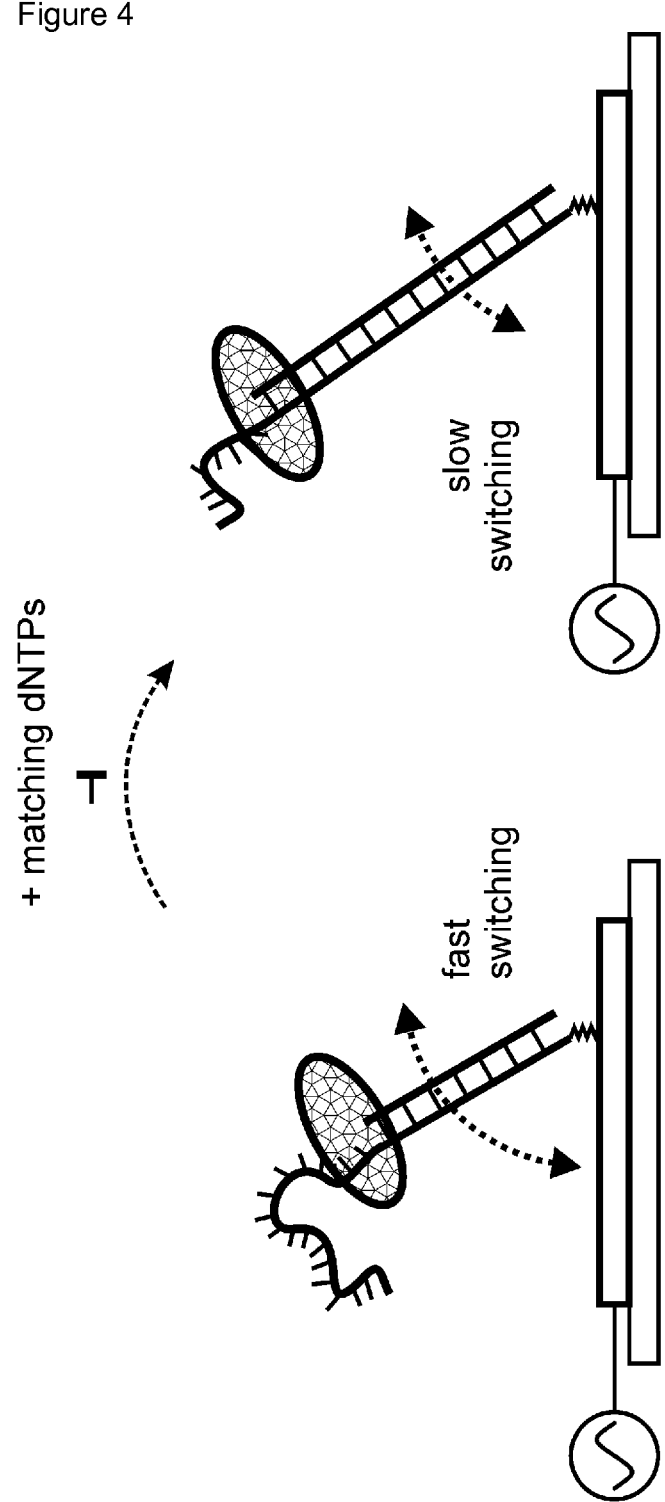

According to the present invention, electro-switchable biosensors were surprisingly found to be useful for sequencing of target sequences and for identifying a nucleotide at a defined position of a target polynucleotide. As shown in FIG. 4, electro-switchable biosensors are useful to measure the slowing-down of the DNA switching dynamics, and therefore to measure a decrease in the velocity of a hybridized polynucleotide's movement in the electric field generated by the alternate current voltage upon incorporation of nucleotides by the polymerase.

The movement of the hybridized polynucleotide, which is end-tethered according to the invention, is understood as the switching between a "standing" and "lying" orientation with respect to the electro-switchable biosensor surface, as illustrated in FIG. 4.

It could now be surprisingly shown that nucleotide sequencing and identifying a nucleotide at a defined position of a polynucleotide can be achieved by determining the switching dynamics, and therefore velocity of the hybridized nucleotides' movements in the electric field. The switching dynamics, and therefore velocity of a hybridized DNA's movement can be measured e.g. as described in Examples 2 and 3 either in a time-resolved or frequency-resolved measurement mode. The term "switching dynamics" is used with respect to (i) the temporal course of the upward or downward switching motions (as inferred from time-resolved measurements), as a measure of the velocity, or (ii) the characteristic frequency response curve of the fluorescence modulation amplitude (as inferred from frequency-resolved measurements), as a measure of the velocity. Therefore, the velocity of the hybridized polynucleotide's movement in the electric field is in a preferred embodiment determined by a time-resolved or frequency-resolved measurement mode. Both modes are known to a skilled person as described in EP 2 434 021 A1 and EP 2 192 401 A1, and are also summarized below in Example 2.

In the initial state, the polynucleotide, in particular the DNA, exhibits "fast switching dynamics", which depend on the polynucleotide length, in particular DNA length (absolute and relative length of the single and double stranded segments) and the type of polymerase which is bound to the polynucleotide, in particular DNA (see FIG. 4, left).

When the layer is incubated with one or more matching nucleotides (dNTPs for DNA), the polymerase incorporates the matching dNTPs along the DNA and converts part of the target polynucleotide strand from a single to a double strand. The double stranded segment is elongated and the polymerase moves upward along the DNA.

Consequently, the switching dynamics, and therefore the velocity of the DNA/polymerase complex decreases, because (i) as the (comparably large) polymerase moves up along the DNA it also moves away from the pivot point of the double stranded DNA lever on the surface and thus must be dragged over a longer distance through the solution as the DNA orientation is switched up and down. When the ds-DNA lever length increases, the total rotational hydrodynamic friction of the DNA/polymerase complex increases (ii) as the double-stranded segment of the DNA is elongated, its hydrodynamic friction increases.

It is understood that above arguments equally apply for other polynucleotides, such as RNA.

A biosensor is understood as analytical device, used for the detection of an analyte that combines a biological component with a physicochemical detector. According to the present invention, the biological component in the methods and devices of the present invention are the primer and the hybridized target polynucleotides, respectively, and the velocity of the polynucleotides is detected.

A hybridized polynucleotide according to the present invention is a single polynucleotide complex (often called duplex) established by a non-covalent, sequence-specific interaction between complementary portions of strands of the primer and the target polynucleotide, and optionally the distinct linker molecule. Preferably, the complementary portions of these strands have a length of about 5, 10, 15, 20, 21, 22, 23, 24, 25, 26, 27, 28, 29, 30 or more nucleotides, and the complementary portions exhibit a match of at least 90%, 95%, 96%, 97%, 98%, 99% or 100%. A match is understood as A-T, or A-U pairing, respectively, or C-G pairing. In case of mismatches, such mismatches may be insertions, deletions, and/or mismatching nucleotides.

An electro-switchable biosensor is a bio sensor wherein an alternating current voltage can be applied to the surface of the biosensor and the velocity of the movement of a biomolecule in the electric field can be determined. In the present invention, the velocity of the movement of the hybridized polynucleotide is determined.

Such preferred suitable electro-switchable biosensor is shown in FIG. 1. The electro-switchable biosensor further comprises in a preferred embodiment a non-conducting solid-phase carrier (1), which is in particular a glass or plastic carrier, which serves as a flat support for a quenching layer/working-electrode (2).

The quenching-layer (2) comprises, preferably consists of, an energy-accepting material that suppresses the light emission of a photoluminescence emitter (10) when said emitter approaches the layer.

In a preferred embodiment, the quenching layer is a metal layer, in particular a gold or platinum layer, more preferably a gold film of 5 to 300 nm thickness, or an organic layer, in particular a conducting polymer, a layer comprising a dye and organic molecules, wherein the organic molecules are energy-accepting molecules or a dye-sensitized matrix.

Conducting polymers are organic polymers that conduct electricity. Suitable conducting polymers are known to a skilled person and include for example polyacetylene, polypyrrole, polyaniline, Poly(p-phenylene vinylene) and poly (pyrrole)s (PPY).

The layer comprising a dye and organic molecules, wherein the organic molecules are energy-accepting molecules, is preferably embedded in a polymer matrix.

A dye-sensitized matrix is understood as layer comprising a dye and organic molecules, wherein the organic molecules are energy-accepting molecules wherein such layer is embedded in a polymer matrix. The dye-sensitized matrix is preferably a blend of a photo-inactive material (e.g. a polymer) and a photoactive compound (dye, e.g. Cy5), the latter of which acts as an energy-acceptor (photoluminescence quencher.

In a yet further preferred embodiment, the quenching layer is a single conducting film, or a plurality, in particular 2 to $10^5$, 2 to $10^6$, 2 to $10^7$, 2 to $10^8$, or 2 to $10^9$ of individually addressable microelectrodes which are arrayed on a single solid-phase carrier.

In a preferred embodiment of the present invention, photoluminescence is used in order to determine the hybridized polynucleotide's movement in the electric field. In such embodiment, a marker which can emit photoluminescence is used. According to the present invention, a marker which can emit photoluminescence is also called PL-Emitter.

Photoluminescence (PL) describes the phenomenon of light emission from any form of matter after the absorption of photons (electromagnetic radiation). It is one of the forms of luminescence (light emission) and is initiated by photo-excitation, which is understood as excitation by photons.

In a preferred embodiment, photoluminescence is fluorescence and/or the marker (PL Emitter) is a fluorescent marker. In this embodiment, the absorption spectrum of the quenching layer overlaps with the emission spectrum of the PL-emitter, so that non-radiative energy transfer is possible.

The PL emitter or marker (10) is either attached to one of the nucleotide strands, in particular nucleotide strands, preferably DNA strands, (6, 7, 8, 9) of the primer, linker or target polynucleotide, or the polymerase (13). Alternative positions of the marker are indicated in FIG. 1 as stars with full and dashed lines, respectively. PL-emission is stimulated by excitation light from a light source (14) which is collimated onto the surface by imaging optics or laser deflection optics (15). For the spatially resolved detection of PL light, imaging optics (15) and a photo-detector (16) are used.

For the application of alternating electric fields, the quenching layer/working electrode (2) is connected to a counter electrode (11) via a voltage source (12). The hybridized target polynucleotide, in particular hybridized DNA, is repelled by negative electrode voltages and attracted to the electrode for positive applied voltages. The waveform of the applied alternating voltage can be square-ware, sine, or any other. The working and the counter electrodes are integrated in a fluidic compartment filled with electrolyte solution (not shown). The solution above the surface may be exchanged by some form of a liquid handling device, for instance a pump connected to a micro fluidic channel, or (automated) pipetting procedures (not shown).

In a preferred embodiment of the present invention the quenching layer (and working electrode) (2) is a gold, indium-tin-oxide, or platinum electrode.

In a yet further preferred embodiment, the light source (14) is a light emitting diode (LED), a laser, or halogen lamp.

In a yet further preferred embodiment, the imaging optics or laser deflection optics (15) is comprised of objectives, lenses, bandpass and dichroic filters and beam splitters, or is a standard epi-fluorescence microscope, or is a fluorescence imaging system, for example as being used in commercially available systems for DNA sequencing.

In a yet further preferred embodiment, the photo-detector (16) is a CCD (charged coupled device), or photomultiplier, or photodiode detector. Such photo-detectors are well-known to a skilled person.

The voltage source (12) is in a preferred embodiment a standard voltage source suitable for applying a typical voltage between 0 and +/−1.0 V to the working electrode.

Notably, the applied voltage depends on the dielectric characteristics as thickness, or dielectric constant of the SAM spacer layer where present or any other dielectric layer in the system and may be significantly higher than an absolute value of 1.0 V if required. It is noted that the applied voltage is used to polarize the surface, but not to drive any Faradaic currents (charge transfer) across the interface which would damage the molecular layer.

The target polynucleotide strand, in particular target DNA strand, to be analyzed or sequenced (9) is bound to the surface by hybridizing to a primer oligonucleotide strand (6) via a dedicated primer/adapter region (8), and which primer is bound via a linker to the electro-switchable-surface, preferably to the quenching layer. The binding of the primer to the electro-switchable surface can be accomplished in one preferred embodiment by covalent linkage of the primer to the electro-switchable surface (see Example 3.3, FIG. 5A and FIG. 1B). In a further preferred embodiment, the binding of the to primer to the electro-switchable surface can be accomplished by covalent linkage of a distinct linker molecule to the electro-switchable surface, wherein the linker molecule comprises a primer binding domain (7), which preferably is an oligonucleotide, an alkanylene chain, and a domain binding the linker to the biosensor surface (4, 5) (see FIG. 1A). In this latter embodiment, the primer is not covalently bound to the electro-switchable surface, in order to allow for movement in the electrical field. In case of a covalent linkage of the primer to the electro-switchable surface, the primer may be linked via a linker to the electro-switchable-surface, wherein the linker comprises a primer binding domain, which is in this embodiment a covalent linkage to the primer, an alkanylene chain, and a domain binding the linker to the biosensor surface.

In one preferred embodiment, the linker is a distinct linker molecule, which comprises a primer binding domain (7), an alkanylene chain, a domain binding the linker to the electro-switchable surface (4, 5). In this embodiment, the primer binding domain (7) preferably is an oligonucleotide. In this embodiment, the primer is not covalently bound to the electro-switchable surface.

Thus, the primer strand is bound, preferably at one end, by a linker (4, 5), which forms a strong, preferably covalent, bond (5) to the surface (for instance, a sulfur—gold bond). This results in end-tethered primer molecules: either the primer is itself covalently attached to the electro-switchable surface, or the primer is bound via a distinct linker molecule to the electro-switchable surface; in both embodiments, the primer is bound by one linker to the electro-switchable surface.

In a preferred embodiment, the linker is bound covalently to the electro-switchable surface. In another preferred embodiment, the primer is bound non-covalently to the electro-switchable surface.

In case of a distinct linker molecule, the surface-near part of the primer strand preferably forms a rigid nucleotide duplex, in particular DNA duplex, with a the primer binding domain of the linker, as reinforcement oligonucleotide strand (7), which is bound to the surface via a dedicated linker (4). In this embodiment, the primer binding domain (7) and target polynucleotide (8) are in one embodiment separate strands (i.e. without covalent linkage); in another embodiment, they are covalently bound, in particular by joining them using a ligase prior, during or after the method of the invention.

The linker is preferably flexible or forms an unhindered pivot point, so that the hybridized target polynucleotide, in particular DNA, can switch its orientation with respect to the surface. The switching movement is indicated in FIGS. 1A and 1B as (17).

In a preferred embodiment, the primer/adapter region (8) has a length in the range from 5 to 100 nucleotides, preferably from 10 to 50 nucleotides.

In a yet further preferred embodiment, the primer binding domain (7) in case of a distinct linker molecule is an oligonucleotide that has a length in the range from 5 to 100 nucleotides, preferably from 10 to 50 nucleotides.

In one preferred embodiment, the linker comprises an alkanylene chain. For example, an alkanethiol, in particular mercatohexanol ($(CH_2)_6$—SH), see Example 3) may be used for binding the primer to a gold layer. The terminal thiol group reacts with the gold surface to from a gold-sulfur bond. In such example, the resulting —$(CH_2)_6$— moiety represents the alkanylene chain, and the sulfur atom (or —SH group, respectively, prior to the reaction with the gold layer of the biosensor) represents the domain binding the linker to the biosensor moiety.

The alkanylene chain is preferably a straight-chain or branched, preferably straight-chain alkanylene group, with 1 to 20, more preferably 3 to 10, even more preferably 4, 5, 6, 7, 8, 9 or 10 carbon atoms, which is optionally interrupted by 1, 2, or 3 atoms selected from O, Se, S, and N, and/or wherein the alkanylene group optionally further comprises 1, 2 or 3 double or triple bonds between C atoms. Even more preferably the alkanylene chain is selected from —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, and —$(CH_2)_{10}$—. In a preferred embodiment, the alkanylene chain is a saturated chain and does not comprise double or triple bonds between C atoms. In case double bounds or triple bonds are present between C atoms, these are preferably used to bind the linker to the biosensor moiety and therefore represent a domain capable of binding the linker to the biosensor moiety.

The domain capable of binding the linker to the biosensor moiety, preferably to the quenching layer, is preferably a moiety that comprises or consists of one, two three or more the following functional groups prior to the reaction with the bio sensor or quenching layer, respectively: aldehyde, ketone, thiol, amine, carboxyl, hydrazine, hydrazide, hydroxyl, glycan, azide, alkyne, alkene, and silicone. It is understood that the resulting linkage to the biosensor depends on the chemical nature of the biosensor or quenching layer, respectively. In case of gold as biosensor surface material and/or quenching layer material, the use of a thiol, resulting in the formation of a gold-sulfur bond, is preferred.

The incorporation of nucleotides which match the target polynucleotide, in particular DNA, sequence in a complementary manner is performed by a polymerase (13), which binds to the hybridized target polynucleotide, in particular DNA, at the single-stranded/double-stranded junction.

An optional self-assembled monolayer (SAM, 3) can be used in a preferred embodiment to backfill the space next to and between hybridized target polynucleotide molecules (6, 7). The SAM-forming molecules feature a chemical headgroup (3a) for covalent coupling to the biosensor surface, preferably quenching layer (2), and a variable tail group. Such self-assembled monolayers as well as their synthesis are for example described in Lahann et al. (2003, Science, 299(5605): 371-374). In Lahann et al., self-assembled monolayers of alkanethiols with charged headgroups were used to realize a surface that can be rendered hydrophobic or hydrophilic by reversing the potential applied to the supporting gold electrode. At positive bias, the negatively charged headgroups are attracted to the surface and the non-polar, hydrophobic alkane-backbone is exposed; at negative bias, the charged headgroups extend away from the surface, effectively rendering it hydrophilic. The SAM-forming molecules are bound to the biosensor surface, preferably quenching layer, preferably by a moiety that comprises or consists of one, two three or more the following functional groups prior to the reaction with the biosensor, preferably quenching layer: aldehyde, ketone, thiol, amine, carboxyl, hydrazine, hydrazide, hydroxyl, glycan, azide, alkyne, alkene, and silicone. It is understood that the resulting linkage to the biosensor depends on the chemical nature of the biosensor. In case of gold as biosensor surface material and/or quenching layer material, the use of a thiol, resulting in the formation of a gold-sulfur bond is preferred. The SAM-forming molecules may be optionally substituted alkane or oligonucleotide molecules.

In a further preferred embodiment, a carboxylic or ethylene glycol moiety, and/or a compound or composition with non-fouling properties and/or protein-repellant properties may be present, covalently or non-covalently bound to the quenching layer. Thus in a preferred embodiment of the invention, the device of the invention further comprises a carboxylic or ethylene glycol moiety, and/or a compound or composition with non-fouling properties and/or protein-repellant properties, covalently or non-covalently bound to the quenching layer. Examples of such compounds or compositions are PEGylated or fluorinated self-assembled monolayers.

In the methods of the invention an alternating current voltage is applied. The voltage applied by the device is preferably one which includes stepwise or continuous change, preferably continuous change. The voltage waveform is not subject to any particular limitation, although sine waves or square waves are generally employed, in particular square waves as shown in Example 3. With regard to the voltage value, it is preferred to use a potential range that has been adjusted so as not to break the bond between the primer and the electro-switchable surface; in the case of a bond between sulfur of the linker and a gold quenching layer, the absolute voltage is typically set to not more than 0.5 V or 1.0 V. Therefore, cases in which the average voltage is 0 V, cases in which the average is a positive value, and cases in which the average is a negative value are all possible.

Although the voltage frequency is not subject to any particular limitation, a frequency range that allows formation of an electrical double layer as a source for the electric field is desirable. As shown in the Examples a frequency of between 0.1 kHz to 100 kHz, in particular of between 1 kHz to 100 KHz are particularly useful.

A primer is a strand of nucleic acid, in particular DNA or RNA, preferably DNA, that serves as a starting point for DNA or RNA, preferably DNA, synthesis. The primer is preferably a DNA primer, as such primers are known to be chemically stable. Typically, the primer is an oligonucleotide having a length of between 5 and 100 nucleotides, preferably from 10 to 50 nucleotides.

The present method is used for identifying a nucleotide at a defined position of a target polynucleotide. A polynucleotide molecule or nucleic acid is a biopolymer composed of 5 or more nucleotide monomers covalently bonded in a chain, preferably straight chain. DNA (deoxyribonucleic acid) and RNA (ribonucleic acid) are examples of polynucleotides. In a preferred embodiment, the target polynucleotide is a DNA. With the method of the invention, a nucleotide at a defined position may be identified. For example, it may be determined whether position X of the coding region of a certain gene or ORF is A, T, G or C.

A nucleotide is composed of a nucleobase, a five-carbon sugar, typically either ribose in RNA or 2-deoxyribose in DNA, and one or more phosphate groups. Without the phosphate group, the nucleobase and sugar compose a nucleoside. A nucleotide can thus also be called a nucleoside monophosphate. The phosphate groups form bonds with either the 2, 3, or 5-carbon of the sugar, with the 5-carbon site most common. Cyclic nucleotides form when the phosphate group is bound to two of the sugar's hydroxyl groups. Nucleotides contain either a purine or a pyrimidine base. Ribonucleotides are nucleotides in which the sugar is ribose. Deoxyribonucleotides are nucleotides in which the sugar is deoxyribose.

Nucleobases are nitrogen-containing biological compounds (nitrogenous bases) found within deoxyribonucleic acid (DNA), ribonucleic acid (RNA), nucleotides, and nucleosides. The primary nucleobases are cytosine (in DNA and RNA), guanine (in DNA and RNA), adenine (in DNA and RNA), thymine (in DNA) and uracil (in RNA), abbreviated as C, G, A, T, and U, respectively.

In DNA, the purine bases are adenine and guanine, while the pyrimidines are thymine and cytosine. RNA uses uracil in place of thymine. Adenine usually pairs with thymine by 2 hydrogen bonds, while guanine pairs with cytosine through 3 hydrogen bonds, each due to their unique structures.

In a preferred embodiment of the method of the present invention, determining the velocity of the hybridized polynucleotide's movement in the electric field is performed by measuring photoluminescence using a photodetector, particularly wherein the primer, the polymerase and/or the target polynucleotide, and/or optionally the distinct linker molecule is labeled with a fluorescent marker or a colloidal semiconductor nanocrystal.

The use of photoluminescence, in particular fluorescence is preferred, as this allows the determination of the orientation of the end-tethered hybridized polynucleotides via fluorescence energy transfer in connection with the quenching layer. Using fluorescence energy transfer, it is possible to observe the persistent switching of DNA molecules between standing and lying conformations over millions of cycles. In competition with the emission of a photon upon irradiation, the optically excited state on the dye may decay by a non-radiative energy transfer (ET) process to the quenching layer, in particular metal layer, which quenches the marker's fluorescence close to the surface. Therefore, quenching occurs preferentially when the hybridized target polynucleotide is in a "lying" position with respect to the quenching layer, whereas quenching occurs less when the hybridized target polynucleotide is in a "standing" position with respect to the quenching layer (see FIG. 4 for the positions).

According to the invention, a quenching layer is a layer which decreases the fluorescence intensity of a marker or PL-Emitter, in particular by non-radiative energy transfer.

In a preferred embodiment the colloidal semiconductor nanocrystal is suitable for fluorescence measurements, such as CdSe quantum dots.

A quantum dot is a nanocrystal made of semiconductor materials that are small enough to display quantum mechanical properties, specifically its excitons are confined in all three spatial dimensions.

Colloidal semiconductor nanocrystals are synthesized from precursor compounds dissolved in solutions by methods known to a skilled person. Typical dots are made of binary alloys such as cadmium selenide, cadmium sulfide, indium arsenide, and indium phosphide. Dots may also be made from ternary alloys such as cadmium selenide sulfide. These quantum dots can contain as few as 100 to 100,000 atoms within the quantum dot volume, with a diameter of 10 to 50 atoms. As indicated below, the use of CdSe quantum dots is preferred. CdS quantum dots may be obtained by reacting $Cd^{2-}$ and $S^{2-}$ ions in aqueous solution. Due to the intrinsic thermodynamical instability of colloidal suspensions, a stabilizing agent, for example sodium polyphosphate, is preferably added to the reacting system. Subsequent surface passivation with $Cd(OH)_2$ may be carried out to improve luminescence. The quantum dots may further be functionalized to allow bioconjugation and labeling of the nucleotides or polymerase according to the invention.

A nanocrystal is understood as crystalline nanoparticle with at least one dimension <100 nm, preferably at least two dimensions <100 nm, more preferably 3 dimensions <100 nm.

According to step b) of the method of the invention, the primer is contacted under conditions conducive to the formation a hybridized polynucleotide and the elongation of the primer, with the target polynucleotide and a polymerase capable of elongating the primer.

The target polynucleotide, in particular DNA, may be obtained from various sources, depending on the intended application. For example, PCR-amplified DNA fragments may be used, or fragmented and/or sheared genomic DNA, for example obtained by sonification. Such methods are known to a skilled person. The target polynucleotide, in particular DNA, can be prepared by various conventional methods. For example, target polynucleotide can be prepared as inserts of any of the conventional cloning vectors, including those used in conventional DNA sequencing. Extensive guidance for selecting and using appropriate cloning vectors is found in Sambrook et al., Molecular Cloning: A Laboratory Manual, Second Edition (Cold Spring Harbor Laboratory, New York, 1989), and like references. Sambrook et al. and Innis et al., editors, PCR Protocols (Academic Press, New York, 1990) also provide guidance for using polymerase chain reactions to prepare target polynucleotides. Cloned or PCR-amplified target polynucleotides can be used according to the present invention. For such polynucleotides, the cloning and PCR methods can be used to append dedicated primer/adapter region (8) to which the primer can hybridize.

In a preferred embodiment, sheared DNA fragments from a subject organism, for example human, are treated to provide blunt ends, then ligated to at least one oligonucleotide, which represents dedicated primer/adapter region (8), by methods known to a skilled person.

As indicated for step a) of the method of the invention, the primer is bound to an electro-switchable surface. Therefore, the contacting with the target polynucleotide and a polymerase may typically achieved by adding fluids, in particular solutions, comprising the target polynucleotide and a polymerase, either in a single or separate solutions to the bound primers. In Example 3, the target polynucleotide was added in a first step, and as a further step, a solution comprising polymerase was added. If the components are added as separate solutions, also additional washing steps, preferably using a buffer solution, may be performed. The target polynucleotide and the polymerase are preferably added as a buffered solution(s).

The polymerase capable of elongating the primer is in a preferred embodiment a DNA polymerase such as DNA polymerase I, II or III. In other aspects, suitable polymerases include a DNA dependent RNA polymerase and reverse transcriptase such as an HIV reverse transcriptase. Specific examples include T7 DNA polymerase, Φ29 DNA polymerase, T5 DNA polymerase, E. coli DNA polymerase I, T4 DNA polymerase, T7 RNA polymerase and Taq DNA polymerase. Those of skill in the art will know of other polymerases suitable for use in the present invention.

One of skill is thoroughly familiar with the theory and practice of nucleic acid hybridization and primer selection. Gait, ed. Oligonucleotide Synthesis: A Practical Approach, IRL Press, Oxford (1984); W. H. A. Kuijpers Nucleic Acids Research 18(17), 5197 (1994); K. L. Dueholm J. Org. Chem. 59, 5767-5773 (1994); S. Agrawal (ed.) Methods in Molecular Biology, volume 20; and Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, N. Y., provide a basic guide to nucleic acid hybridization.

Primers in combination with a polymerase are used to sequence a target polynucleotide and/or to identify a nucleotide at a defined position. Primer length is selected to provide for hybridization to complementary template DNA. Primers may be designed to hybridize to known internal sites on the subject target DNA. Alternatively, the primers can bind to synthetic oligonucleotide adaptors joined to the ends of target DNA by a ligase as explained above to yield the dedicated primer/adapter region (8).

A skilled person is aware of conditions conducive to the formation a hybridized polynucleotide and the elongation of the primer, with the target polynucleotide and a polymerase capable of elongating the primer. Such conditions typically comprise a reaction mixture obtained after contacting of step b) comprising an aqueous buffer medium, which is optimized for the particular polymerase. In general, the buffer includes a source of monovalent ions, a source of divalent cations and a buffering agent. Any convenient source of monovalent ions, such as KCl, K-acetate, $NH_4$-acetate, K-glutamate, $NH_4Cl$, ammonium sulfate, and the like may be employed, where the amount of monovalent ion source present in the buffer will typically be present in an amount sufficient to provide for a conductivity in a range from about 500 to 20,000, usually from about 1000 to 10,000, and more usually from about 3,000 to 6,000 microhms.

The divalent cation may be magnesium, manganese, zinc and the like, where the cation will typically be magnesium. Any convenient source of magnesium cation may be employed, including $MgCl_2$, Mg-acetate, and the like. The amount of Mg ion present in the buffer may range from 0.5 to 20 mM, but will preferably range from about 1 to 12 mM, more preferably from 2 to 10 mM and will ideally be about 5 mM.

Representative buffering agents or salts that may be present in the buffer include Tris, Tricine, HEPES, MOPS and the like, where the amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to 9.5, where most preferred is pH 7.6 at 25° C. Other agents which may be present in the buffer medium include chelating agents, such as EDTA, EGTA and the like.

Under such conditions, the target polynucleotide will hybridize to the primer resulting in a hybridized target polynucleotide, as for example shown in FIGS. 1A and 1B. Such hybridized target polynucleotide may also comprise the distinct linker molecule as shown in FIG. 1A.

According to step c) of the present invention, the primer is then contacted with one or more nucleoside triphosphate containing identical nucleobases of one type. This may typically be achieved by adding an optionally buffered solution containing one or more nucleoside triphosphate molecules containing identical nucleobases of one type; i.e. one or more molecules dATP, or one or more molecules dTTP, or one or more molecules dCTP, or one or more molecules dGTP in case of DNA. A washing step is optionally applied prior to and/or after adding such solution to the primer. As the conditions now allow primer elongation, the nucleoside triphosphate is incorporated into the hybridized polynucleotide and the primer is elongated, if its nucleobase is complementary to a nucleobase at the corresponding position on the target polynucleotide, whereas the nucleoside triphosphate is not incorporated into the hybridized polynucleotide and the primer is not elongated, if its nucleobase is not complementary to a nucleobase at the corresponding position on the target polynucleotide.

As explained above and as shown in Example 3, the incorporation of the nucleotide results in larger hybridized target polynucleotide, which exhibits a different velocity, in particular decreased velocity in an electric field when an alternating current voltage is applied. As also explained above, the different velocity, in particular decreased velocity, can be determined in case of a fluorescent marker by determining the quenching by the quenching layer as a measure of the orientation of the hybridized target polynucleotide. In case the velocity remains unamended, no nucleoside triphosphate was incorporated. In this case, steps b) and c) of the method of the present invention are then repeated with one or more nucleoside triphosphates containing identical nucleobases of a type different from that used in previous step(s) c), until elongation is detected. When repeating the steps, the nucleoside triphosphate of one type is preferably removed and/or the hybridized target polynucleotide is washed prior to and/or after the addition of nucleoside triphosphates containing different identical nucleobases, as explained in Example 3.2.

The velocity changes, in particular decreases, by a characteristic unit value upon elongation of the target polynucleotide by a single nucleotide. If, due to a stretch of homonucleotides along the target polynucleotide, the nucleoside triphosphate of one type is incorporated multiple times, the velocity changes, in particular decreases by a corresponding multiple of the characteristic value.

Thereby, by performing the method of the invention, the nucleotide at the corresponding position of the target polynucleotide can be identified.

As explained above, the method is in particular useful for determining a nucleotide in a target DNA. Also, the by far most common naturally-occurring nucleobases in DNA are A, C, G and T. Therefore, in a further preferred embodiment of the method of the present invention, the target polynucleotide is DNA and the nucleobases used in step(s) c) are selected from A, C, G and T.

However, the method of the invention may also be applied to RNA as target polynucleotide. The skilled person is aware how to select suitable polymerase therefore. Also, the by far most common naturally-occurring nucleobases in RNA are A, C, G and U. In such further preferred embodiment of the method of the present invention, the target polynucleotide is RNA and the nucleobases used in step(s) c) are selected from A, C, G and U.

As explained above, step b) involves the generation of a hybridized target polynucleotide from a target polynucleotide and a primer. In order to allow hybridization, the target polynucleotide is preferably single-stranded, or rendered single-stranded prior to step b). This can be achieved by methods known to a skilled person, for example by DNA denaturing agents like urea. Thus, in another preferred embodiment of the method of the present invention, the target polynucleotide is single-stranded or rendered single-stranded prior to step b).

As described above, it is possible to use unmodified, naturally occurring nucleoside triphosphates for the methods of the present invention, such as dATP, dCTP, dGTP and dTTP in the case of DNA. Therefore, in a further preferred embodiment of the method of the present invention, the nucleoside triphosphates are not labeled.

In an alternative embodiment of the present invention, it is possible to use labeled nucleoside triphosphates. "Labeled" or "label" in the context of "labeled nucleoside triphosphates" is understood as a chemical moiety bound to a nucleoside triphosphate, which binding may be covalent or non-covalent, preferably covalent, with the prerequisite that the labeled nucleoside triphosphate is capable of incorporation into a target polynucleotide to which a primer is hybridized, under conditions conducive to the formation of a hybridized polynucleotide and elongation of the primer, using a polymerase capable of elongating the primer. A labeled nucleoside triphosphate is therefore a modified nucleoside triphosphate. In one preferred embodiment, the label of a labeled nucleoside triphosphate is a detectable label. In another preferred embodiment, the label of a labeled nucleoside triphosphate is not a detectable label.

Labeled derivatives of nucleoside triphosphates which are reversible terminators overcome some problems occurring with natural, unmodified nucleoside triphosphates for accurately deciphering the homopolymeric regions of nucleotide templates. For example, it is possible to use reversible terminators, which are nucleoside triphosphate molecules wherein the 3'—OH group is capped with a small chemically reversible moiety, such as an azidomethyl, allyl or 2-nitrobenzyl group. The incorporation of such derivative temporarily terminates the polymerase reaction. After detection of the incorporation of the nucleoside triphosphate, the capping group may be released and the nucleoside triphosphate thereby deprotected, allowing further elongation. Such label increases weight of the nucleoside triphosphate.

Also phosphate-labeled nucleoside triphosphates may be used which contain a detectable label on any of its phosphate positions. The label, e.g., a dye, can be attached to the nucleoside triphosphates by a linker. The label or linker can be attached to the phosphate atom by a phosphorus-oxygen, phosphorus-sulfur, phosphorus-nitrogen, or phosphorus-carbon bond, for example, dUTP-PEG8-P2-AlexaFluor633. The nucleoside triphosphate can also incorporate a polyethylene glycol (PEG) moiety in addition to a dye label.

For example, the nucleoside triphosphate can be a PEG-modified NTP or dNTP (e.g., dNTP with a PEG linker) with or without a further label. Suitable PEG-moieties are moieties of the formula —$((CH_2)_2$—$O)_n$—, with n=1 to 20, preferably n=1, 2, 3, 4, 5, 6, 7, 8, 9, or 10.

One example of a phosphate-labeled nucleotide is a γ-labeled nucleotide. The term "γ-labeled" refers to a detectable label or an undetectable linker attached to any of the 3 phosphates on the nucleoside triphosphates. The term γ-phosphate-labeled nucleoside triphosphate refers to any nucleotide that contains a detectable label on its terminal, e.g., γ-phosphate, position. Preferably, nucleotide triphosphates are used, however other phosphates such as mono-, di-, tri, tetra-, penta-, and polyphosphate esters can also be used, wherein the label is preferably attached to the terminal phosphate, but may be attached to non-terminal phosphates. Certain labeled nucleoside triphosphates suitable for use in the present invention include, but are not limited to, labeled nucleotides disclosed in for example, U.S. Pat. Nos. 6,232,075, 6,306,607, 6,936,702, 6,869,764, U.S. Patent Publication No. US2005/0042633, U.S. patent application Ser. No. 11/118,031, filed Apr. 29, 2005, Ser. No. 11/154,419, filed Jun. 15, 2005 and 60/648,091, filed Jan. 28, 2005.

Such labels on the nucleoside triphosphates, which increase the charge, size and/or weight of the nucleoside triphosphates, may be used to increase the characteristic value of velocity decrease measured upon incorporation of a nucleoside triphosphate into the hybridized target polynucleotide. Thereby, sensitivity may be enhanced. In this embodiment, it is preferred that the nucleoside triphosphates of all types are labeled with identical labels.

Thus, in another preferred embodiment of the method of the present invention, the nucleoside triphosphates of all types are labeled with identical labels, particularly labels increasing the charge, size and/or weight of the nucleoside triphosphates.

In yet another preferred embodiment of the method of the present invention, the label of the nucleobases triphosphate is polyethylene glycol (PEG).

Alternatively, the nucleoside triphosphates of all types are labeled, wherein the label differs between the different types of nucleobases, but is identical for one type of nucleobases. Such embodiment may be useful to detect the characteristic value of velocity decrease measured upon incorporation of specific type of nucleoside triphosphate into the hybridized target polynucleotide.

In another preferred embodiment of the method of the present invention, the nucleoside triphosphates of all types are labeled, wherein the label differs between the different types of nucleobases, but is identical for one type of nucleobases, particularly labels increasing the charge, size and/or weight of the nucleoside triphosphates.

The method of the invention allows identifying a nucleotide at a defined position of a target polynucleotide and/or sequencing of a target polynucleotide without employing labeled nucleoside triphosphates. Therefore, in another preferred embodiment, the nucleoside triphosphates used in the methods and devices of the invention are not labeled.

As indicated above, the use of photoluminescence, in particular fluorescence is particularly preferred for the methods of the present invention. In order to determine the velocity of the end-tethered hybridized target polynucleotide's movement in the electric field, the quenching effect observed with certain materials like gold may be used. In competition with the emission of a photon upon irradiation, the optically excited state on the marker, in particular fluorescent dye, may decay by a non-radiative energy transfer (ET) process to the quenching layer, in particular metal layer, which quenches the marker's fluorescence close to the surface.

Therefore, in a yet further preferred embodiment of the method of the present invention, the biosensor surface comprises a quenching layer, particularly wherein the quenching layer is a metal layer, especially a gold or platinum layer.

In another preferred embodiment of the method of the present invention, the linker comprises a primer binding domain (such as an oligonucleotide), an alkanylene chain and a domain binding the linker to the biosensor surface, particularly to a quenching layer. Such linker which is a distinct linker molecule and wherein the primer binding domain is an oligonucleotide, is illustrated in FIG. 1A. According to another preferred embodiment, as exemplified in Example 3.3 and as shown in FIG. 1B, the linker is covalently attached to the primer molecule. In this embodiment, the primer binding domain is a covalent bond to the primer. The alkanylene chain may be a —$(CH_2)_6$— moiety, as described in Example 3.3.

According one preferred embodiment as shown in the Examples 1 and 3.3, the linker is bound to the quenching layer of the biosensor surface, which is a gold layer, and the domain binding the linker to the biosensor surface is sulfur, which forms a bond to Au of the layer. In the Examples, such bond is formed by the reaction of mercatohexanol with the gold layer.

The primer is preferably of a length which allows hybridization to the target polynucleotide under conducive conditions.

Thus, in another preferred embodiment of the method of the present invention, the primer has a length in the range of from 5 to 100 nucleotides, preferably from 10 to 50 nucleotides.

The method of the invention is suitable for determining a nucleotide at a defined position or for sequencing a target polynucleotide of a broad range of origin or length, and the target polynucleotide may be obtained by various methods like PCR, cloning and/or genomic DNA fragmentation, as explained above. In order to allow primer binding to a target polynucleotide, in particular DNA, of unknown sequence, synthetic oligonucleotide adaptors can be joined to the ends of target DNA by a ligase as explained above to yield the dedicated primer/adapter region (8). Preferably, these oligonucleotide adaptors are added to the 3' end of the target polynucleotide. This yields a 3'-terminal end complementary to the primer. In order to allow hybridization of the primer, the complementary region has a length of from 5 to 100 nucleotides, preferably from 10 to 50 nucleotides.

Thus in a yet further preferred embodiment of the method of the present invention, the target polynucleotide has a length in the range of from 5 to 10,000 nucleotides, preferably from 10 to 5,000 nucleotides, more preferably from 20 to 1,000, especially from 20 to 500, 400, 300, 200 or 100 nucleotides and/or (ii) has a 3'-terminal end complementary to the primer, especially wherein the complementary region has a length of from 5 to 100 nucleotides, preferably from 10 to 50 nucleotides.

In a yet further preferred embodiment of the method of the present invention, the primer, the polymerase and/or the target polynucleotide is labeled with a fluorescent marker, particularly a cyanine dye, especially Cy2, Cy3, Cy3B, Cy3.5, Cy5, Cy5.5, Cy7 or Cy7.5, preferably Cy3, or a colloidal semiconductor nanocrystal, such as a CdSe quantum dot.

Such embodiments are again illustrated in FIGS. 1A and 1B, and in Example 3.3. In Example 3.3, the target polynucleotide was labeled with the fluorescent marker Cy3.

Cyanine dyes, like Cy2, Cy3, Cy3B, Cy3.5, Cy5, Cy5.5, Cy7 or Cy7.5, preferably Cy3 are well-known in the art. Cyanine dyes are synthetic dyes belonging to polymethine group.

The labeling of the target polynucleotide with a marker molecule, in particular a fluorescent marker molecule may be achieved by treating the target polynucleotide to provide blunt ends, where needed, and then ligating to the target polynucleotide an oligonucleotide labeled with the marker, by methods known to a skilled person. The primer and/or the distinct linker molecule may be labeled with the marker directly, by methods known to a skilled person. Similarly, methods for labeling a polymerase with a marker, in particular fluorescent marker are known.

In another preferred embodiment of the method of the present invention, the polymerase is processive. For example, Bst DNA polymerase from *Bacillus stearothermophilus* may be used. A polymerase is understood to be processive if it catalyzes at least about 50 consecutive reactions without releasing its substrate. This ensures that the polymerase remains attached to the DNA strand and catalyzes a considerable number of reactions to incorporate nucleotides.

As explained above, the method of the invention is suitable for identifying a nucleotide at a defined position of a target polynucleotide. By repeating steps b) to e) of the method of identifying a nucleotide at a defined position of a target polynucleotide of the invention one or more times, the subsequent nucleotides at the positions of the target polynucleotide directly following the defined position of a target polynucleotide, can be identified in 5' to 3' direction. Thereby, the sequence, or part of the sequence of the target polynucleotide can be determined. Washing steps may optionally be included before and/or after a certain method step in particular in order to remove nucleoside triphosphates previously present.

In another embodiment, the present invention relates to a method for determining the sequence or part of the sequence of a target polynucleotide comprising:

i) providing an electro-switchable biosensor comprising
  a primer capable of forming a hybridized polynucleotide with the target molecule, wherein the primer is linked to a electro-switchable surface, and
  means for applying an alternating current voltage and determining the velocity of the hybridized polynucleotide's movement in the electric field;

ii) carrying out steps b) to e) of the method of the invention defined above to identify a nucleotide at a defined position of a target polynucleotide, and iii) repeating steps b) to e) of the method of identifying a nucleotide at a defined position of a target polynucleotide of the invention one or more times to identify one or more subsequent nucleotide(s) at the position(s) of a target polynucleotide directly following the defined position of a target polynucleotide, thus identifying the nucleotides at the corresponding positions of the target polynucleotide, thereby determining the sequence or part of the sequence of a nucleotide.

As explained in Example 3.2, steps b) to e) in step iii) of the above method of the invention can be repeated until the velocity of the hybridized target polynucleotide's movement in the electric field does not change anymore, irrespective of the type of added nucleoside triphosphate. In this case, the whole target polynucleotide strand has been converted from a single- to a double-strand. Thus, the whole target polynucleotide sequence starting from the primer matching position was determined. Alternatively, only part of the sequence may be determined.

Typically, the above method of the invention is repeated at most 1,000 times, preferably at most 500 times, more preferably at most 400, 300, 200 or 100 times, in order to ensure accuracy of sequencing, but in principle, it is also possible to repeat the method more than 1,000 times.

In a further preferred embodiment of the method of the present invention, steps b) to e) in step iii) of the above method of the invention are repeated at most 1,000 times, preferably at most 500 times, more preferably at most 400, 300, 200 or 100 times.

Depending on the number of repetitions of steps b) to e) in step iii) of the above method of the invention and the site of primer binding, either the whole sequence or part thereof of the target polynucleotide can be determined.

The preferred embodiments disclosed and described for the method of identifying a nucleotide at a defined position of a target polynucleotide of the invention also apply to the method for determining the sequence or part of the sequence of a target polynucleotide of the invention.

The methods of the present invention are useful for a variety of biotechnological, veterinary, agricultural and medical applications where determining sequences or parts thereof is of importance, like whole-genome analysis, identification of single nucleotide polymorphism, targeted sequencing or in the diagnosis of genetic disorders, such as cancer.

Therefore, in a further preferred embodiment, the method of the invention is used in whole-genome analysis, identification of single nucleotide polymorphism, targeted sequencing or in the diagnosis of genetic disorders, such as cancer.

In yet another embodiment, the present invention relates to a device adapted for performing a method of the invention, the device comprising:

(i) a support carrying an electro-switchable biosensor surface comprising a quenching layer;
(ii) a linker capable of binding a primer to the biosensor surface;
(iii) means for separately storing the nucleoside triphosphates of each type;
(iv) means for applying an alternating current voltage to the biosensor surface;
(v) means for separately transporting the nucleoside triphosphates of each type to the detection spot(s) on the biosensor surface;
(vi) means for applying an alternating current voltage to the bio sensor surface; and
(vii) means for determining the velocity of a bound primer's movement in the electric field generated by the application of the alternating current voltage to the electro-switchable surface.

A preferred device with components (i), (ii), (iv), (vi) and (vii) is illustrated in FIGS. 1A and 1B as well as the Figure legend thereof.

A device comprising an electro-switchable biosensor with components (i), (ii), (iv), (v), (vi) and (vii) is described in EP 2 434 021 A1. The components (i), (ii), (iv), (v) as described in EP 2 434 021 A1 are suitable for a device of the present invention, and it is hereby explicitly referred to the device comprising the components (i), (ii), (iv), (v), (vi) and (vii) and the components (i), (ii), (iv), (v), (vi) and (vii) disclosed in EP 2 434 021 A1 as preferred components of the device of the present invention. The content of EP 2 434 021 A1 relating to an electro-switchable bio sensor is therefore incorporated by reference.

The device is adapted for performing a method of the invention. Thus, the device is suitable for performing at least one method of the invention. The device of the invention comprises at least one electro-switchable biosensor surface.

The device comprises a support carrying an electro-switchable biosensor surface comprising a quenching layer. As described above, the support is preferably a non-conducting solid-phase carrier (1), which is in particular a glass or plastic carrier, which serves as a flat support for the quenching layer (2). The support is preferably non-conducting, as the quenching layer is conducting.

The quenching-layer (2) comprises, preferably consists of, an energy-accepting material that suppresses the light emission of a photoluminescence emitter (10) when said emitter approaches the layer.

In a preferred embodiment, the quenching layer is a metal layer, in particular a gold or platinum layer, more preferably a gold film of 5 to 300 nm thickness, or an organic layer, in particular a conducting polymer, a dye-sensitized matrix or layer comprising a dye and organic molecules, wherein the organic molecules are energy-accepting molecules.

In a further preferred embodiment of the present invention the quenching layer (and working electrode) (2) is a gold, indium-tin-oxide, or platinum electrode.

The device further comprises means for applying an alternating current voltage to the biosensor surface.

For the application of alternating electric fields, the quenching layer/working electrode (2) is connected to a counter electrode (11) via a voltage source (12). The hybridized polynucleotide, in particular hybridized DNA is repelled by negative electrode voltages and attracted to the electrode for positive applied voltages. The waveform of the applied alternating voltage can be square-ware, sine, or any other. The working and the counter electrodes are integrated in a fluidic compartment filled with electrolyte solution (not shown). The solution above the surface may be exchanged by some form of a liquid handling device, for instance a pump connected to a micro fluidic channel, or (automated) pipetting procedures (not shown).

The voltage source (12) is in a preferred embodiment a standard voltage source suitable for applying a typical voltage between 0 and +/−1.0 V to the working electrode, preferably for applying a voltage between 0 and more than +/−1.0 V.

The device further comprises means for determining the velocity of a bound primer's movement in the electric field generated by the application of the alternating current voltage to the electro-switchable surface.

Typically, such means comprise a light source (14) which preferably is a light emitting diode (LED), a laser, or halogen lamp, imaging optics or laser deflection optics (15) which preferably is comprised of objectives, lenses, bandpass and dichroic filters and beam splitters, or is a standard epifluorescence microscope, or is a fluorescence imaging system, for example as being used in commercially available systems for DNA sequencing, and a photo-detector (16) which preferably is a CCD, or photomultiplier, or photodiode detector.

Such means are described above in more detail.

In a preferred embodiment of the present invention, photoluminescence is used in order to determine the hybridized polynucleotide's movement in the electric field, as described above.

In such embodiment, the means for determining the velocity of a bound primer's movement in the electric field generated by the application of the alternating current voltage to the electro-switchable surface preferably further comprises a marker which can emit photoluminescence (PL emitter), even more preferably the means further comprise a fluorescent emitter.

The device further comprises a linker capable of binding a primer to the biosensor surface.

As described above for the methods of the invention, the binding of the to primer to the electro-switchable surface can be accomplished in one preferred embodiment by covalent linkage of the primer to the electro-switchable surface (see Example 3.3, FIG. 1B and FIG. 5A) and in a further preferred embodiment by covalent linkage of a distinct linker molecule to the electro-switchable surface, wherein the linker molecule comprises a primer binding domain (7) (which preferably is an oligonucleotide), an alkanylene chain, and a domain binding the linker to the biosensor surface (4, 5) (see FIG. 1A).

Thus, in case of a covalent linkage of the primer to the electro-switchable surface, the linker molecule comprises an alkanylene chain, and a domain binding the linker to the biosensor surface, as well as a primer binding domain, which primer binding domain is a covalent linkage to the primer if the primer is already covalently bound to the biosensor surface, or is a functional group capable of forming a covalent bond with the primer in case the primer is not bound yet to the biosensor surface.

In another preferred embodiment, the linker is a distinct linker molecule, which comprises a primer binding domain (7), an alkanylene chain, and a domain binding the linker to the electro-switchable surface (4, 5). In this embodiment, the primer binding domain is preferably an oligonucleotide.

Thus, the primer strand can then in turn be bound, preferably at one end, by a linker (4, 5), which forms a strong, preferably covalent, bond (5) to the surface (for instance, a sulfur-gold bond). This results in end-tethered primer molecules.

In one preferred embodiment, the primer is itself covalently attached to the electro-switchable surface. In another preferred embodiment the primer is bound via a distinct linker molecule to the electro-switchable surface. In both embodiments, the primer is bound by one linker to the electro-switchable surface.

The linker is preferably flexible or forms an unhindered pivot point, so that the DNA strand can switch its orientation with respect to the surface.

In a yet further preferred embodiment, the primer binding domain (7) in case of a distinct linker molecule is an oligonucleotide that has a length in the range from 5 to 100 nucleotides, preferably from 10 to 50 nucleotides.

The electro-switchable biosensor further comprises means for separately storing the nucleoside triphosphates of each type.

As explained above, it is important that nucleoside triphosphate molecule of only one type is added is added in step c) of the method of identifying a nucleotide at a defined position. Therefore, the device of the invention contains means for separately storing the nucleoside triphosphates of each type, in order to apply them separately when performing the method. Preferably, the nucleoside triphosphate molecules are stored separately as buffered solutions, more preferably as aqueous and/or sterilized buffered solutions. Suitable means for storing separately are containers, wells, cavities, tubes, or capillary tubes. Such containers, cavities, or wells may comprise, preferably consist of various materials like an organic polymer, glass or metal. The tubes or capillary tubes may be may comprise, preferably consist of various materials like an organic polymer or glass. The containers, wells, cavities, tubes, capillary tubes may be colored or colorless, transparent, semi-transparent, or non-transparent, and/or may be of the same or different color, in particular of different color. The container may be of different shape. The containers, wells, cavities, tubes, or capillary tubes may be designed to allow ongoing refilling or to allow refilling only when the device is not operative or for replacement of the means for storing as a unit e.g. for refilling. In the case of replacement of the means for storing, the means may be designed to replace the means, in particular containers, wells, cavities, tubes, capillary tubes for each nucleoside triphosphate of one type separately, or for replacing the whole unit of separately stored nucleotide triphosphates.

The device further comprises means for separately transporting the nucleoside triphosphates of each type to the detection spot(s) on the biosensor surface. According to the invention, a "detection spot" is understood as an electrode which is functionalized with electro-switchable DNA on the biosensor surface.

When performing the methods of the invention, nucleoside triphosphates need to be transported to the detection spot(s) on the biosensor surface. This allows rinsing with the respective nucleoside triphosphates of the microelectrodes to which hybridized polynucleotide(s) is/are bound. Transportation may be achieved by means known to a skilled person, like pipetting, application via capillary tubes and the like. It is important that the means allow for separate transportation, which means that each type of nucleoside triphosphate is transported in temporal, preferably temporal and spatial separation.

In a preferred embodiment, the device further contains fluidic components, such as microfluidic channels, tubes, pumps, and/or containers, by which the solution above the biosensor surface, in particular detection spot(s) can be exchanged. In a particularly preferred embodiment, the device further contains microfluidic channel(s), which is/are more preferably located above the microelectrodes. In a particularly preferred embodiment, the device further contains container(s).

In a further preferred embodiment, the device further contains a plurality of microfluidic channels and/or containers, in particular up to one microfluidic channel and/or container per microelectrode. Also, a single microfluidic channel and/or container may be present for a plurality of microelectrodes.

In a preferred embodiment, the device of the invention or the means (i) of the device of the invention comprises a plurality, in particular 2 to $10^5$, 2 to $10^6$, 2 to $10^7$, 2 to $10^8$, or 2 to $10^9$, of electro-switchable biosensor surfaces as defined above.

For example, the quenching layer of the electro-switchable bio sensor may be present as a single conducting film, or a plurality of individually addressable microelectrodes which are arrayed on a single solid-phase carrier.

In a further preferred embodiment, the device of the invention, or the means (vii) of the device of the invention contains a plurality of photo-detectors, or a single photo-detector, which is a CCD.

In a further preferred embodiment, the device of the invention or the means (vi) of the device of the invention contains a single voltage source. The output of the voltage source may be connected to the single microelectrodes, if required.

For the device of the present invention, also the preferred embodiments disclosed above for the methods of the invention apply.

In another preferred embodiment, the device of the invention is for simultaneously analyzing a plurality of target polynucleotides with the methods of the invention. Depending on the primers, target polynucleotide and quenching layer film or individually addressable microelectrodes which are arrayed on a single solid-phase carrier, 1, 2 or more, e.g. up to $10^5$, $10^6$, $10^7$, $10^8$, or $10^9$ or more polynucleotides may be analyzed at the same time. This makes the device useful for high-throughput sequencing and for genomic analyses.

The device of the invention is in particular useful for performing the methods of the invention. Thereby, the device can be used to determine the sequence or part of the sequence of a target polynucleotide and/or for identifying a nucleotide at a defined position of a target polynucleotide.

In another embodiment, the present invention relates to the use of an electro-switchable surface for determining the sequence or part of the sequence of a target polynucleotide and/or for identifying a nucleotide at a defined position of a target polynucleotide.

The primers and oligonucleotides, e.g. in linkers may be made synthetically using conventional nucleic acid synthesis technology. Purification of oligonucleotides, where necessary, is typically performed by either native acrylamide gel electrophoresis or by anion-exchange HPLC. The sequence of the synthetic oligonucleotides can be verified using the chemical degradation method of Maxam and Gilbert (1980) in Grossman and Moldave (eds.) Academic Press, New York, Methods in Enzymology 65:499-560.

FIGURE LEGEND

FIG. 1: depicts the experimental setup for devices and methods of the invention: a non-conducting solid-phase carrier (1) (e.g. glass or plastic) serves as a flat support for a quenching-layer/working-electrode (2). The quenching-layer (2) consists of an energy-accepting material that suppresses the light emission of a photoluminescence emitter (10) when said emitter approaches the layer. In a preferred embodiment, the quenching layer is a metal layer (in particular a gold film of 5-300 nm thickness) or an organic layer (e.g. a conducting polymer, a layer comprising a dye and organic molecules, wherein the organic molecules are energy-accepting molecules, or a dye-sensitized matrix). The marker (here: PL emitter) (10) is preferably an organic fluorescent dye molecule or a colloidal semiconductor nanocrystal. It is either attached to one of the polynucleotide strands, in particular DNA strands (6, 7, 8, 9), or the polymerase (13). Alternative positions of the PL emitter are indicated as stars with full and dashed lines, respectively. PL-emission is stimulated by excitation light from a light source (14) which is collimated onto the surface by imaging optics or laser deflection optics (15). For the spatially resolved detection of PL light, imaging optics (15) and a photo-detector (16) are used. According to preferred embodiment A, the binding of the primer to the electro-switchable surface can be accomplished by covalent linkage of a distinct linker molecule to the electro-switchable surface, wherein the linker molecule comprises a primer binding domain (7), which preferably is an oligonucleotide, an alkanylene chain, and a domain binding the linker to the biosensor surface (4, 5). According to preferred embodiment B, the binding of the primer to the electro-switchable surface can be accomplished by covalent linkage of the primer to the electro-switchable surface.

Figure 2:
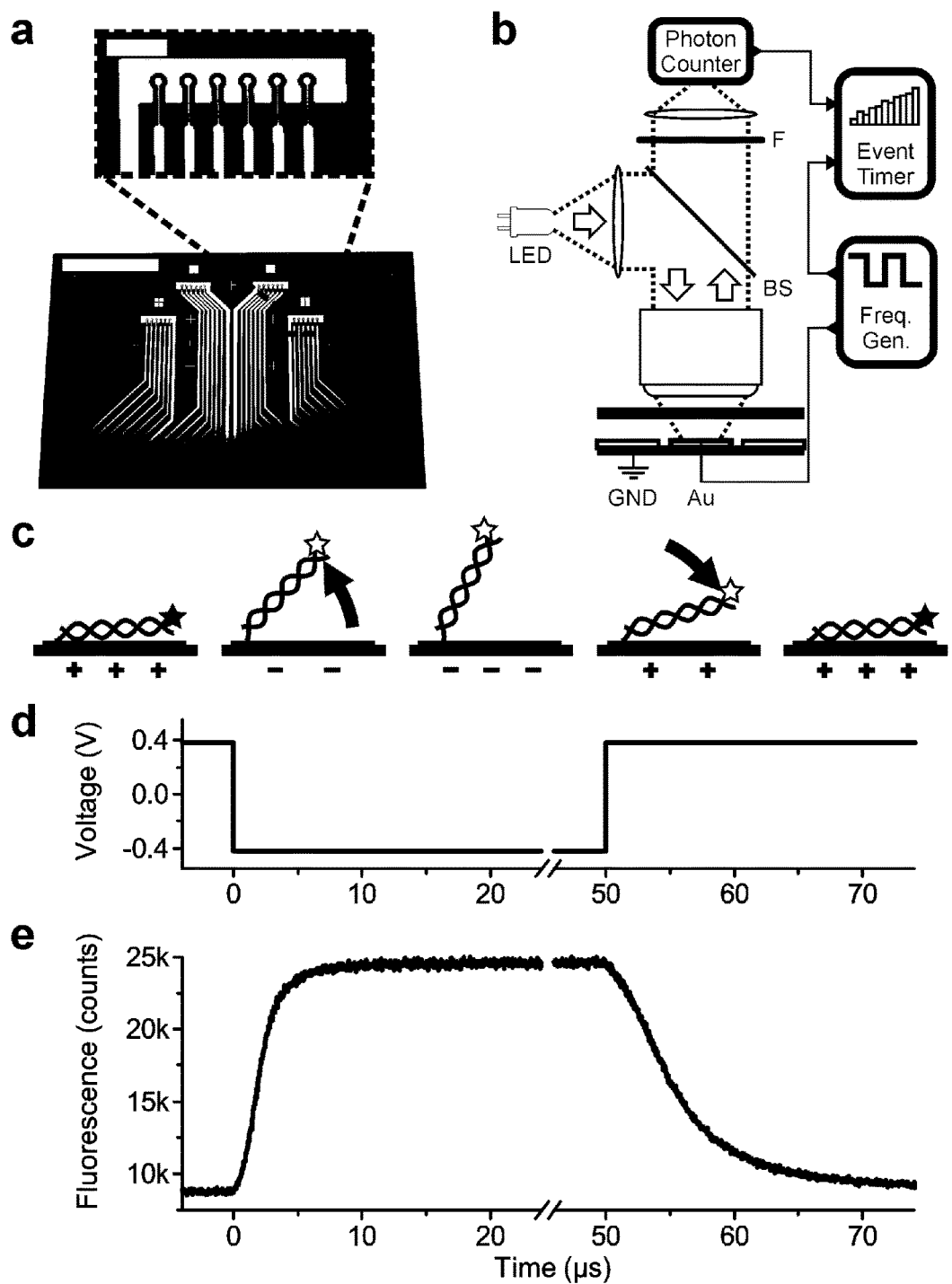

FIG. 2: shows aspects of time-resolved DNA switching measurement: (a) The exemplary bio chip features 24 circular Au microelectrodes (diameter =120 μm) which are individually addressable. Six microelectrodes are arranged together with one Pt counter-electrode in four flow channels (not shown), which are connected via eight holes in the glass carrier. White scale bars are 10 mm and 1 mm (inset). (b) An epi-fluorescence setup is used for the optical detection of DNA orientation in real-time. A frequency generator supplies alternating voltages to the electrodes. This actuates the DNA levers and simultaneously triggers an event timer that records single photons emitted by the fluorescently labeled DNA. (c) Schematic of the electrically induced DNA switching. The fluorophore emission (depicted as a star) is quenched in close proximity to the surface. (d) Square wave voltage which is applied to the Au electrodes vs. Pt (10 kHz) and (e) time-resolved fluorescence response of the 48 bp Cy3-labeled DNA layer.

Figure 3:
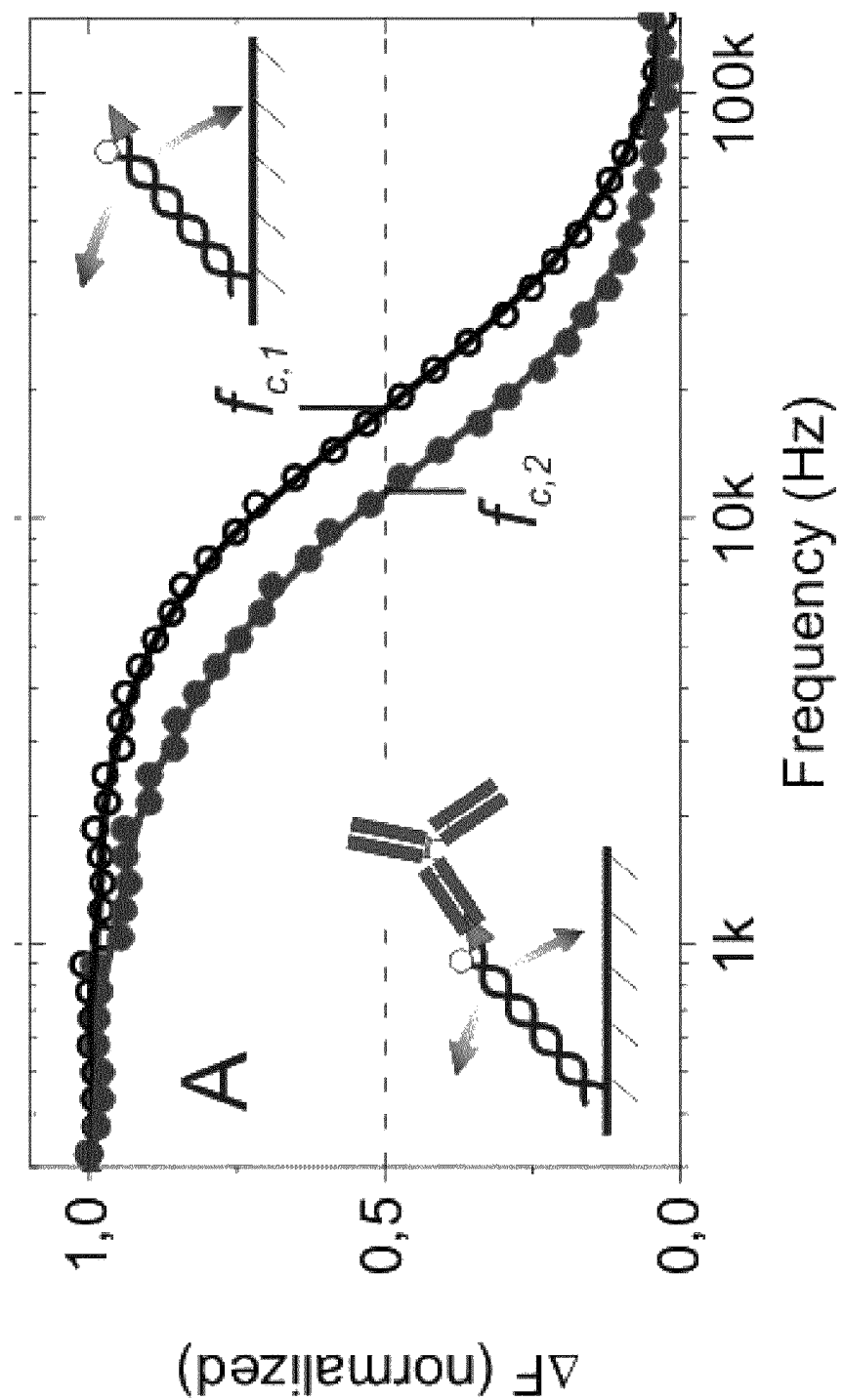

FIG. 3: shows aspects of frequency-resolved measurement: Normalized response of the layer oscillation amplitude AF to increasing frequencies of the applied electrode potential. Frequency response curves were recorded before (open circles) and after (full circles) binding of IgG (sheep) to a DNA-biotin layer under saturation conditions (exposure to a 50 nM anti-biotin IgG solution). $f_{c,1}$ and $f_{c,2}$ mark the cut-off-frequencies before and after antibody binding, respectively.

FIG. 4: illustrates the principle underlying the method of the invention of identifying a nucleotide at a defined position and/or determining the sequence of a target single stranded DNA as exemplary polynucleotide (9):

A slow-down of the DNA switching dynamics and therefore a decrease of the velocity in the electric field upon incorporation of nucleotides by the polymerase is observed. In the initial state, the DNA layer exhibits "fast switching dynamics", which depend on the DNA length (absolute and relative length of the single and double stranded segments) and the type of polymerase which is bound to the DNA (FIG. 4, left). When the layer is incubated with one or more matching nucleotides (dNTPs), the polymerase incorporates the matching dNTPs along the DNA and converts part of the target strand (9) from a single to a double strand. The double stranded segment is elongated and the polymerase moves upward along the DNA. Consequently, the switching dynamics of the DNA/polymerase complex slow down and the velocity of the hybridized target polynucleotide in the electric field decreases.

Figure 5:
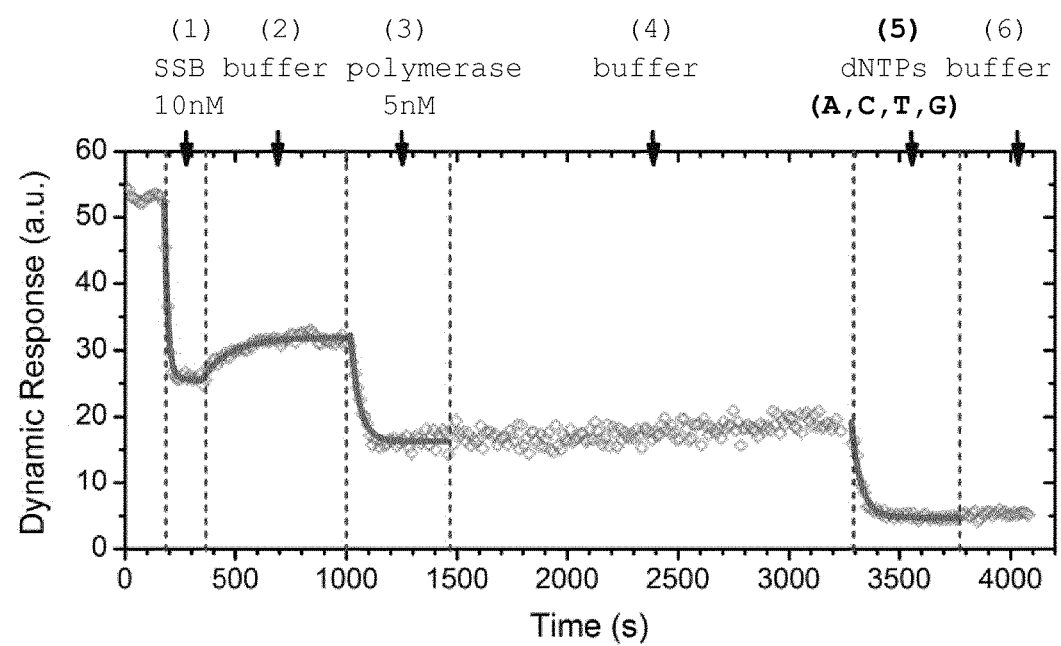

FIG. 5: shows the results of the experiments in Example 3.3. FIG. 5A shows the design of i) the primer single stranded DNA with 40 nucleotides (nt) that was immobilized on a surface via a terminal thiol group and 2) the target DNA to-be-sequenced that was hybridized and thereby bound to the surface-immobilized 40 nt strands via a 40 nt complementary sequence at its 3' end. A Cy3™ fluorescence label was attached to the surface-distal 5' end of the target DNA for optical detection. Abbreviations: seq: sequence; tb-seq: to be sequenced; compl.: complementary. FIG. 5B: determination of the "Dynamic Response" after addition of SSB (single strand binding protein), buffer, polymerase, buffer, dNTPs and buffer, respectively, as described in detail in Example 3.3.

Figure 6:
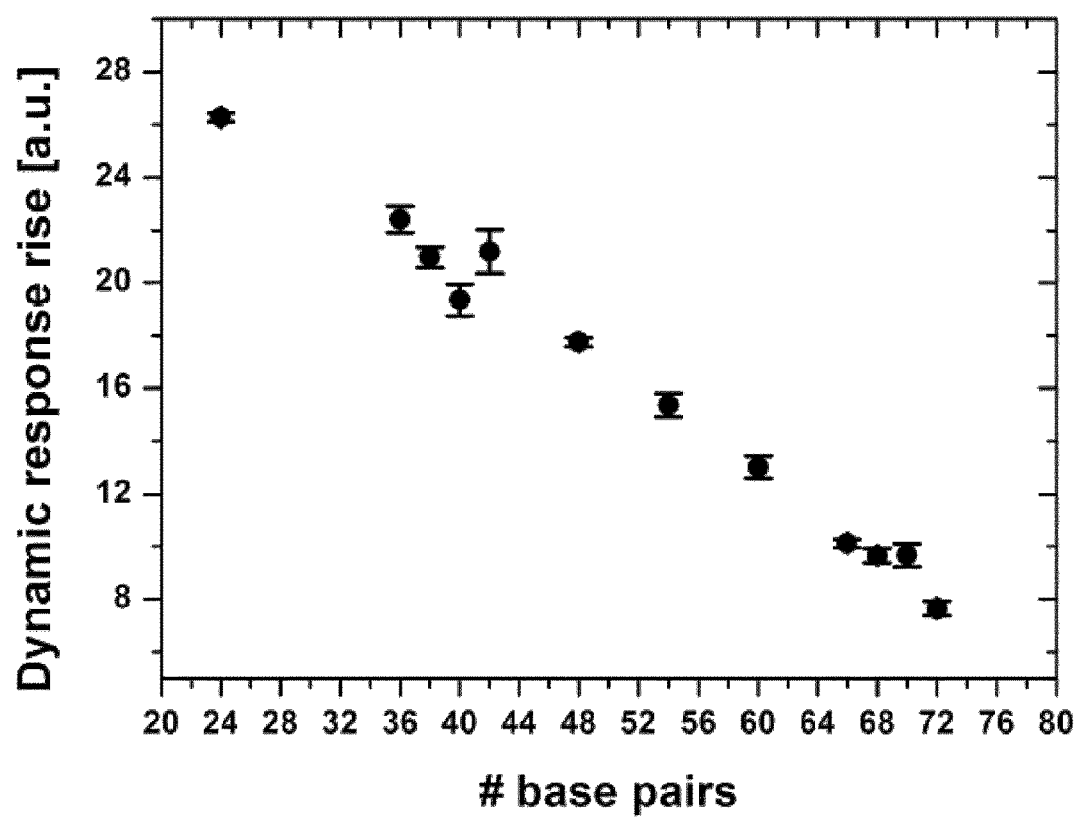

FIG. 6: demonstrates that the Dynamic Response and therefore the velocity of the hybridized target polynucleotide in the electric field depends on the DNA length. The upward (rise) switching motion was measured in time-resolved mode for double stranded oligonucleotide layers of different lengths from 24 to 72 base pairs. No polymerase was used in these experiments, but DNA layers consisting of synthetic oligonucleotides of defined lengths were prepared as a proof-of-concept here. In spite of the fact, that the friction effect of a polymerase was absent in these experiment, the results indicate that single-base extension could be almost be resolved from a "pure" DNA length effect. Thus, the DNA length can be determined from a switching dynamics measurement.

EXAMPLES

Example 1

Setup for Performing a Method of the Invention

Commercial glass carriers were cleaned according to RCA clean procedures. Using standard optical lithography techniques, Au working electrodes (or quenching layer) (2) and Au counter electrodes (11) of 200 nm thickness were evaporated under vacuum onto the glass carriers, using a 10 nm thick Ti film as adhesion layer. The electrode geometry is of minor importance, we used circular working electrodes of 100 μm diameter, surrounded by large rectangular Au counter electrodes of mm dimensions. The electrode structures were sealed within a microfluidic channel made of elastomer and a top glass cover plate. A commercial epi-fluorescence microscope (Olympus) was used for exciting and detecting the fluorescence of Cy3™ dyes (10) ($\lambda_{em}$~570 nm) which were conjugated to the target DNA strand (9) or the polymerase (13). A green LED ($\lambda_{exc}$~530 nm) was used as a light source and a standard photomultiplier with a single photon counting module for detection. Primer oligonucleotides (6) of mixed sequence were obtained commercially with a standard —$(CH_2)_6$—SH linker (4, 5) for immobilization and pre-hybridized in Tris-buffered saline solution (Tris-buffer, pH 7.4, 50 mM NaCl, [oligonucleotide]=1μM). After cleaning the Au surfaces with Piranha solution (mixture of $H_2SO_4$ and $H_2O_2$), the duplexes of the oligonucleotides 6/7 were immobilized via the thiol groups on the Au surface by incubating the electrodes with a 1 μM solution of the oligonucleotides 6/7 in Tris-buffer for up to 1 h. Afterwards, the electrodes were washed with Tris-buffer and incubated with SAM forming reagent (3), i.e. 10 μM mercaptohexanol in Tris-buffer, for at least 1 h. Finally, the electrodes were washed with Tris-buffer and were incubated with target DNA (9) (50 nM in Tris-buffer, 15 min).

Example 2

DNA Switching Measurement

Double stranded DNA oligonucleotides (48 base-pairs) were end-tethered via thiol chemistry to gold microelectrodes, which were arranged in sextuplets within four individually addressable flow channels (V=1 μl) on a glass carrier (FIG. 2a). An epi-fluorescence setup (FIG. 2b) was used to measure the orientation of the DNA levers with respect to the surface. The fluorescence from Cy3 dyes attached to the DNAs' distal ends was gradually quenched when the DNA levers tilted toward the gold surface, due to a non-radiative energy transfer by near-field interactions with the metal. This allowed gauging the distance of the DNAs' upper ends to the surface, and monitoring changes in the DNA orientation in real-time.

The velocity of a polynucleotide's movement can be determined using in particular two approaches, namely by time-resolved measurement and by frequency resolved measurement:

2.1 Time Resolved Measurement (see also EP 2 434 021 A1)

Alternating potentials that are applied to the electrodes repel or attract, respectively, the negatively charged DNA and hence switch the lever orientation between a standing and a lying state (FIG. 1c). Employing time correlated single photon counting (TCSPC) we were able to resolve the upward and downward motion of the DNA levers with 32 ns precision. The delay time of the arrival of a photon at the detector was recorded with respect to the edge of the applied square-wave voltage pulse by an event timer. A fluorescence histogram of satisfactory signal-to-noise ratio was acquired within seconds when driving the approximately 106 DNA levers which were present on one electrode at 10 kHz (FIG. 2d,e).

2.2 Frequency resolved measurement (see also EP 2 192 401 A1 and Nano Letters 4, 1290 (2009))

We examined the switching dynamics by measuring the dependence of the switching amplitude on the frequency of the AC voltage, which drives the molecules into motion.

Typical obtained frequency spectra are presented in FIG. 3. Three distinct regimes could be identified: (i) for low frequencies (<1 kHz) the DNA molecules follow the electrical excitation with maximal efficiency; (ii) in an intermediate regime, the switching amplitude decays; and (iii) for very high frequencies (>100 kHz), the DNA molecules cannot be driven by the applied AC potential anymore. The frequency range (ii) is of particular interest, because it reflects the finite time constant of the switching process. To compare the switching dynamics of different samples, we evaluated the frequency at which the amplitude has decreased to 50% of its initial (low frequency) value and termed it the cut-off frequency $f_c$. For the pristine DNA layer presented in FIG. 3 we found $f_{c,1}$=18 kHz. After the sample has been exposed to the antibody solution and IgG (sheep) bound to the DNA layer, we observed a pronounced shift of the transition regime to lower frequencies, $f_{c,2}$ =11.5 kHz.

Example 3

DNA Sequencing Using an Electro-switchable Biosensor 3.1 Typical Pre-treatment Steps
1. A setup as depicted in FIG. 1A and Example 1 is prepared, except for the target DNA template to be sequenced (9).
2. The target DNA-to-be-sequenced is fragmented into pieces of appropriate length by standard procedures, e.g. by acoustic shearing. Depending on the maximally achievable read-length, this can be for example a few ten basepairs, a few hundred basepairs, or a few thousand basepairs.
3. Adapter/primer sequences (8), which are complementary to the primer strand (6) on the surface, are ligated to the target DNA (9) using standard procedures. During this step, the template DNA may optionally be multiplied by PCR.
4. Optionally, another adapter sequence may be appended on the opposing end of the target DNA. This can, for instance, be used to bind PL-emitter- or marker-labeled oligonucleotides (see FIG. 1).
5. The target DNA with adapters/primers (9+8) is immobilized on the surface via hybridization to the primer strand (6) using standard surface hybridization conditions.
6. A polymerase (13) is bound to the primer duplex 6/8 at the single-stranded/double-stranded junction.

3.2 General Sequencing Steps

An alternating current (AC) voltage (e.g. ±0.4 V, 10 kHz) is applied to the electrode. Driven by the electric repulsion/attraction, the DNA orientation oscillates (switches) between a 'standing' and 'lying' orientation.
1. The surface is incubated with a solution containing nucleotides containing identical nucleobases of one type (e.g. dATP).
2. If the dNTP is complementary to the upcoming unpaired nucleotide along the template DNA next to the single-stranded/double-stranded junction, it will be incorporated by the polymerase. Consequently, the switching dynamics, and therefore velocity, decreases by a characteristic value.
  If, due to a stretch of homo-nucleotides along the template DNA, the dNTP is incorporated multiple times, the switching dynamics, and therefore velocity, decreases by a corresponding multiple of the characteristic value.
  If the dNTP is a mismatch, the switching dynamics, and therefore velocity, stays the same.
3. dNTP which has not been incorporated is removed by exchanging the solution with dNTP-free buffer and optionally washing.
4. Steps 1 and 2 are repeated with a solution containing nucleotides containing different identical nucleobases of one type (e.g. dCTP, dGTP, or dTTP).
5. Steps 1 to 3 can be repeated until the switching dynamics do not change anymore, irrespective of the type of added dNTP. In this case, the whole template DNA strand has been converted from a single- to a double-strand. In this case, the whole target polynucleotide sequence starting from the primer matching position was determined.

3.3 Experimental Sequencing Data

FIG. 5 shows an experiment in which the binding of polymerase and the incorporation of 40 nucleotides is detected in real-time with a time-resolved DNA switching experiment. In the experiment, a method according to the preferred embodiment of FIG. 1A was performed.

Single stranded DNA with 40 nucleotides (nt) was immobilized on a surface via a terminal thiol group (see FIG. 5A). The target DNA to-be-sequenced was hybridized and thereby bound to the surface-immobilized 40 nt strands via a 40 nt complementary sequence at its 3' end (see FIG. 5A). A Cy3™ fluorescence label was attached to the surface-distal 5' end for optical detection.
1. At first, the switching dynamics, and therefore velocity were quantified in a time resolved measurement, yielding a "Dynamic Response" value of ca. 55 arbitrary units (see FIG. 5B). The Dynamic Response (DR) value is used to quantify the swiftness of the switching motion and is defined below in FIG. 6. High DR-values indicate fast switching and high velocity, low DR-values indicate slow switching dynamics and decreased velocity.
2. As single-strand binding protein (SSB) is pumped across the layer, the switching dynamics slow down due to the increase of hydrodynamic drag when SSB binds to the oscillating DNA strands. The Dynamic Response decreases from 55 to 25 units.
3. After pumping buffer solution across the surface to wash out SSB, the DR-value increases again a little bit to ~30 units, indicating that some of the loosely (unspecifically) bound SSB was removed. Most of the SSB, however, remains bound to the DNA layer.

4. When incubating the DNA layer with polymerase (concentration=5E-9 mol/L), the Dynamic Response decreases to ~15 units, signifying that the polymerase has bound to the DNA layer.
5. The Dynamic Response remains unchanged, even after extensively pumping buffer solution over the surface. This indicates that the polymerase remains strongly bound to the DNA.
6. Detection of sequence specific nucleotide incorporation: When a mixture of dATP, dCTP, dGTP, and dTTP (concentration=1 μM) is pumped across the surface, the polymerase incorporates the matching nucleotides. The DNA strands are converted from 'ds40-ss40' to 'ds80' (ds=double strand, ss=single strand) with the polymerase still bound to the surface-distal DNA end. Due to the higher hydrodynamic friction of the fully double stranded DNA, the Dynamic Response decreases to ~5 units.
7. Incubation with buffer solution.

Solid lines in FIG. 5 are single exponential fits, from which the association rates for SSB binding (step 1) and polymerase binding (step 3), as well as the dissociation rate of loosely bound SSB (step 4) are obtained. For step 5, the characteristic exponential constant corresponds to the nucleotide incorporation rate of the polymerase.

FIG. 6 demonstrates that the Dynamic Response depends on the DNA length. The upward (rise) switching motion was measured in time-resolved mode for double stranded oligonucleotide layers of different lengths from 24 to 72 base pairs. No polymerase was used in these experiments, but DNA layers consisting of synthetic oligonucleotides of defined lengths were prepared as a proof-of-concept here. In spite of the fact, that the friction effect of a polymerase was absent in these experiment, the results indicate that single-base extension could be almost be resolved from a "pure" DNA length effect. Thus, the DNA length can be determined from a switching dynamics measurement and therefore the velocity in the electrical field.

The invention claimed is:

1. A method of identifying a nucleotide at a defined position of a target polynudeotide, the method comprising:
a) providing an electro-switchable biosensor comprising a primer capable of forming a hybridized polynucleotide with the target polynucleotide,
wherein the primer is bound via a linker to an electro-switchable surface, and
means for applying an alternating current voltage and determining the velocity of the hybridized polynudeotide's movement in the electric field by measuring photo luminescence using a photo detector;
b) contacting the primer, under conditions conducive to the formation a hybridized polynudeotide and the elongation of the primer, with the target polynudeotide and a polymerase capable of elongating the primer;
c) contacting the primer with one or more nucleoside triphosphate containing identical nucleobases of one type, wherein
the nucleoside triphosphate is incorporated into the hybridized polynucleotide and the primer is elongated, if its nucleobase is complementary to a nucleobase at the corresponding position on the target polynucleotide, and
the nucleoside triphosphate is not incorporated into the hybridized polynudeotide and the primer is not elongated, if its nucleobase is not complementary to a nucleobase at the corresponding position on the target polynudeotide;
d) applying an alternating current voltage to the surface and determining the velocity of the hybridized polynudeotide's movement in the generated electric field by measuring photo luminescence using the photo detector, wherein a decreased velocity is indicative of the incorporation of the nucleoside triphosphate; and
e) if the nucleoside triphosphate is not incorporated into the hybridized polynucleotide, repeating steps c) and d) with one or more nucleoside triphosphates containing identical nucleobases of a type different from that used in previous step(s) c), until elongation is detected, thus identifying the nucleotide at the corresponding position of the target polynucleotide.

2. The method of claim 1, wherein the target polynucleotide is DNA and the nucleobases used in step c) are selected from A, C, G and T, or wherein the target polynucleotide is RNA and the nucleobases used in step c) are selected from A, C, G and U.

3. The method of claim 1, wherein the target polynucleotide is single-stranded or rendered single-stranded prior to step b).

4. The method of claim 1, wherein the nucleoside triphosphates are not labeled.

5. The method of claim 1, wherein the nucleoside triphosphates of all types are labeled with identical labels increasing the charge, size and/or weight of the nucleoside triphosphates.

6. The method of claim 1, wherein the nucleoside triphosphates of all types are labeled, wherein the label differs between the different types of nucleobases, but is identical for one type of nucleobases and the labels are increasing the charge, size and/or weight of the nucleoside triphosphates.

7. The method of claim 1, wherein
a) the biosensor surface comprises a quenching layer, wherein the quenching layer is a metal layer or an organic layer;
b) the linker comprises a primer binding domain, an alkanylene chain and a domain binding the linker to the biosensor surface;
c) the primer has a length in the range of from 5 to 100 nucleotides;
d) the target polynucleotide (i) has a length in the range of from 5 to 10,000 nucleotides, and (ii) has a 3'-terminal end complementary to the primer;
e) one or more of the primer, the polymerase and the target polynucleotide is labeled with a fluorescent marker or a colloidal semiconductor nanocrystal;
f) the polymerase is processive; and
g) the nucleoside triphosphate is labeled with polyethylene glycol (PEG).

8. The method of claim 1, wherein
a) the biosensor surface comprises a quenching layer,
b) the linker comprises a primer binding domain, an alkanylene chain and a domain binding the linker to the quenching layer; a5
c)one or more of the primer, the polymerase and the target polynucleotide is labeled with a fluorescent marker.

9. The method of claim 8, wherein the quenching layer is a metal.

10. The method of claim 8, wherein the fluorescent marker is a cyanine dye selected from the group consisting of Cy2, Cy3, Cy3B, Cy3.5, Cy5, Cy5.5, Cy7 and Cy7.5.

11. A method for determining the sequence or part of the sequence of a target polynucleotide comprising:

i) providing an electro-switchable biosensor comprising
  a primer capable of forming a hybridized polynucleotide with the target polynucleotide, wherein the primer is bound via a linker to an electro-switchable surface, and
  means for applying an alternating current voltage and determining the velocity of the hybridized polynucleotide's movement in the electric field by measuring photo luminescence using a photo detector;
ii) carrying out steps b) to e) of the method as defined in claim 1 to identify a nucleotide at a defined position of the target polynucleotide, and
iii) repeating steps b) to e) of the method as defined in claim 1 one or more times to identify one or more subsequent nucleotide(s) at the position(s) of the target polynucleotide directly following the defined position of the target polynucleotide,
thus identifying the nucleotides at the corresponding positions of the target polynucleotide, thereby determining the sequence or part of the sequence of the target polynucleotide.

12. The method of claim 11, wherein steps b) to e) in step iii) are repeated at most 1,000 times.

\* \* \* \* \*